United States Patent [19]

McCarthy

[11] Patent Number: 5,389,083
[45] Date of Patent: Feb. 14, 1995

[54] GUARDS FOR HYPODERMIC NEEDLE

[75] Inventor: John R. McCarthy, South Boston, Mass.

[73] Assignee: JRM Enterprises, Inc., South Boston, Mass.

[21] Appl. No.: 128,486

[22] Filed: Sep. 28, 1993

Related U.S. Application Data

[63] Continuation-in-part of Ser. No. 4,105, Jan. 13, 1993, abandoned.

[51] Int. Cl.6 ............................................. A61M 5/32
[52] U.S. Cl. ................................. 604/192; 604/263
[58] Field of Search ............... 604/192, 198, 263, 187, 604/232

[56] References Cited

U.S. PATENT DOCUMENTS

| | | |
|---|---|---|
| 2,745,403 | 5/1956 | Goldberg . |
| 2,854,976 | 10/1958 | Heydrich . |
| 3,076,455 | 2/1963 | McConnaughey . |
| 4,643,724 | 2/1987 | Jobe ..................... 604/232 |
| 4,666,435 | 5/1987 | Braginetz ............... 604/198 |
| 4,747,837 | 5/1988 | Hauck ................... 604/198 |
| 4,795,443 | 1/1989 | Permenter et al. . |
| 4,867,746 | 9/1989 | Dufresne . |
| 4,946,447 | 8/1990 | Hardcastle . |
| 4,985,020 | 1/1991 | Kasuya . |
| 4,994,046 | 2/1991 | Wesson et al. . |
| 5,026,356 | 6/1991 | Smith . |
| 5,074,848 | 12/1991 | Burt et al. . |
| 5,087,249 | 2/1992 | Deal . |
| 5,092,461 | 3/1992 | Adam . |
| 5,156,599 | 10/1992 | Ranford et al. .......... 604/198 |

Primary Examiner—John D. Yasko
Attorney, Agent, or Firm—Pearson & Pearson

[57] ABSTRACT

Guards for preventing inadvertent contact with a hypodermic needle. Each guard has a body portion that abuts a syringe barrel and that supports a detachable or integrally formed needle cover. The body also supports a finger grip remotely to the needle cover.

8 Claims, 6 Drawing Sheets

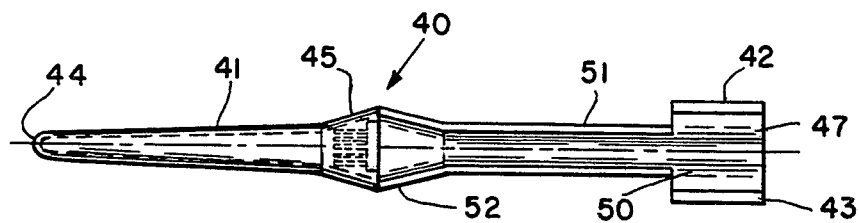
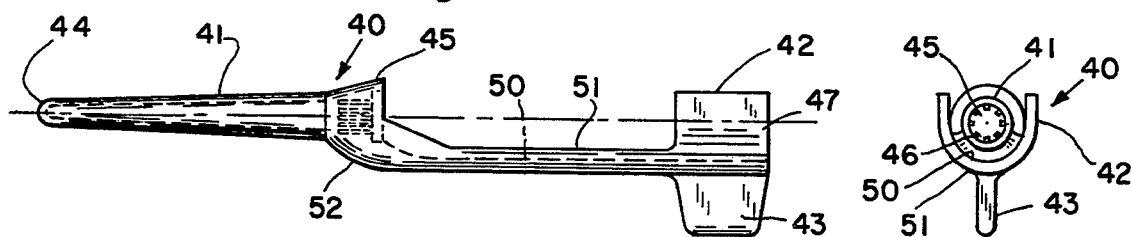
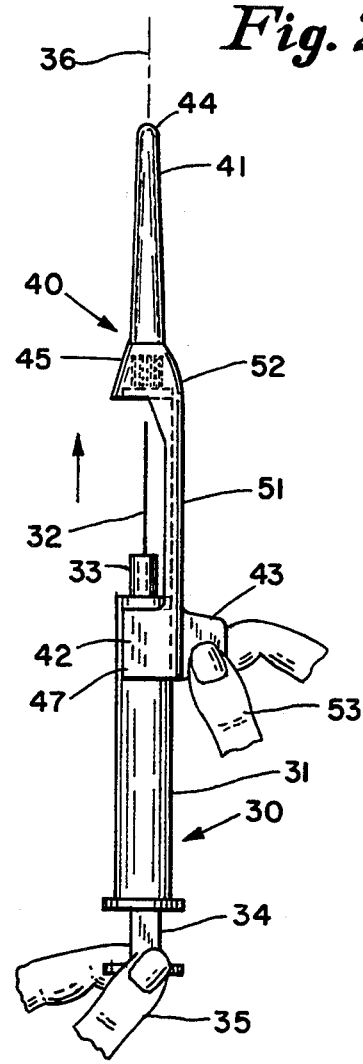
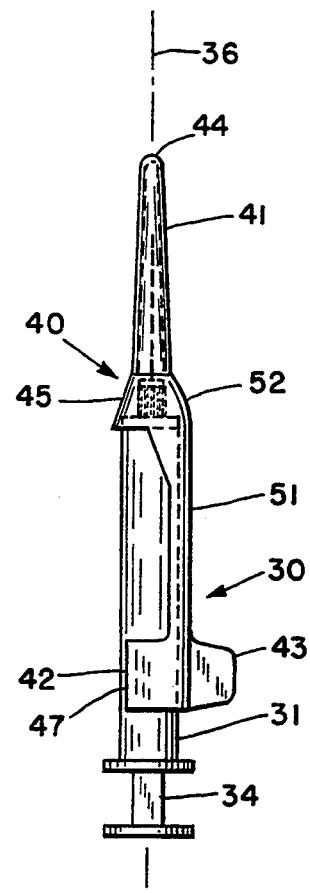
Fig.1.
Fig.2.
Fig.3.
Fig.4.
Fig.5.

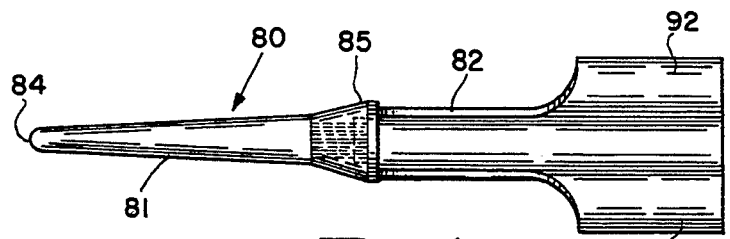
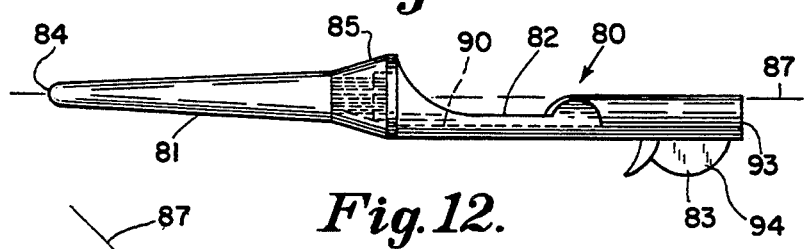
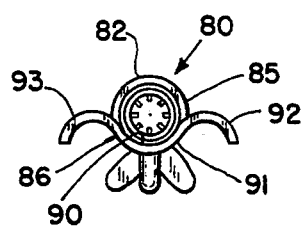
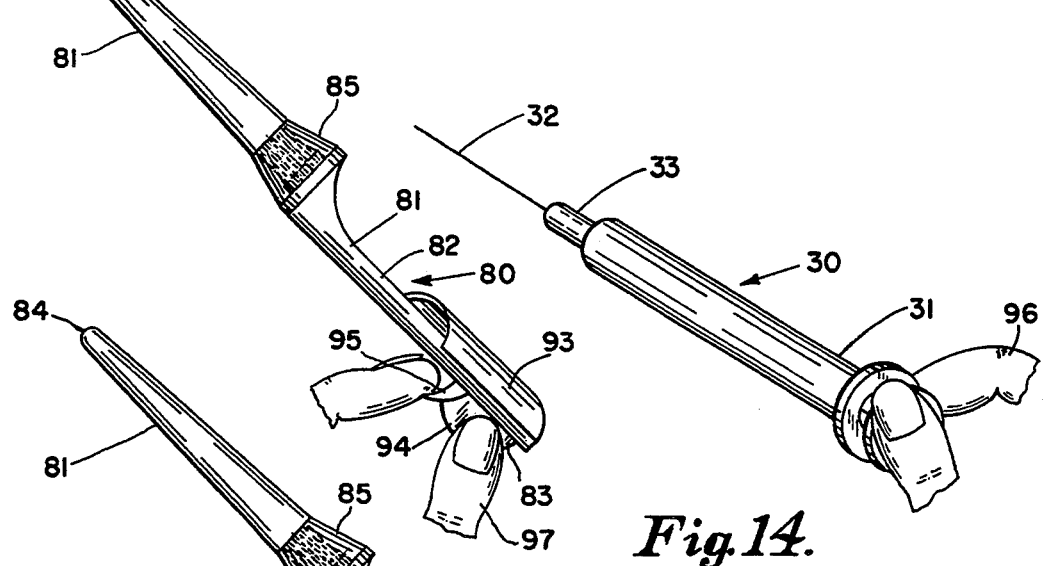
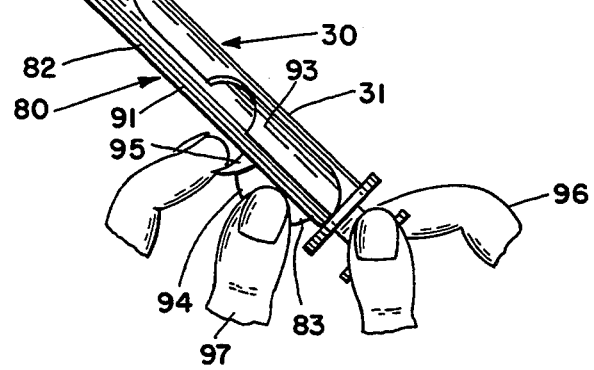

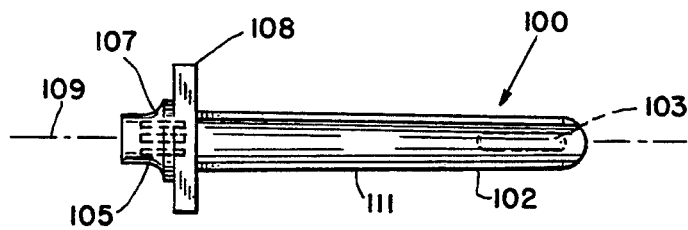
Fig.16.
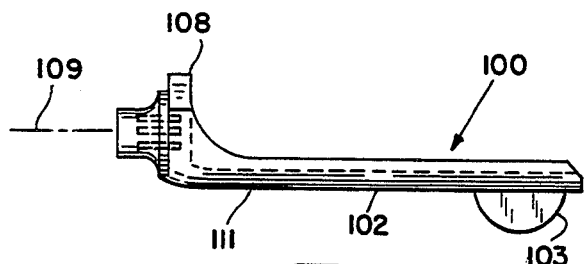
Fig.17.
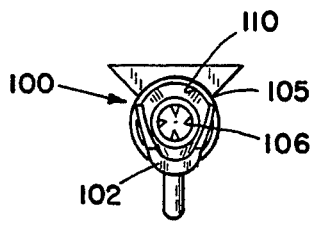
Fig.18.
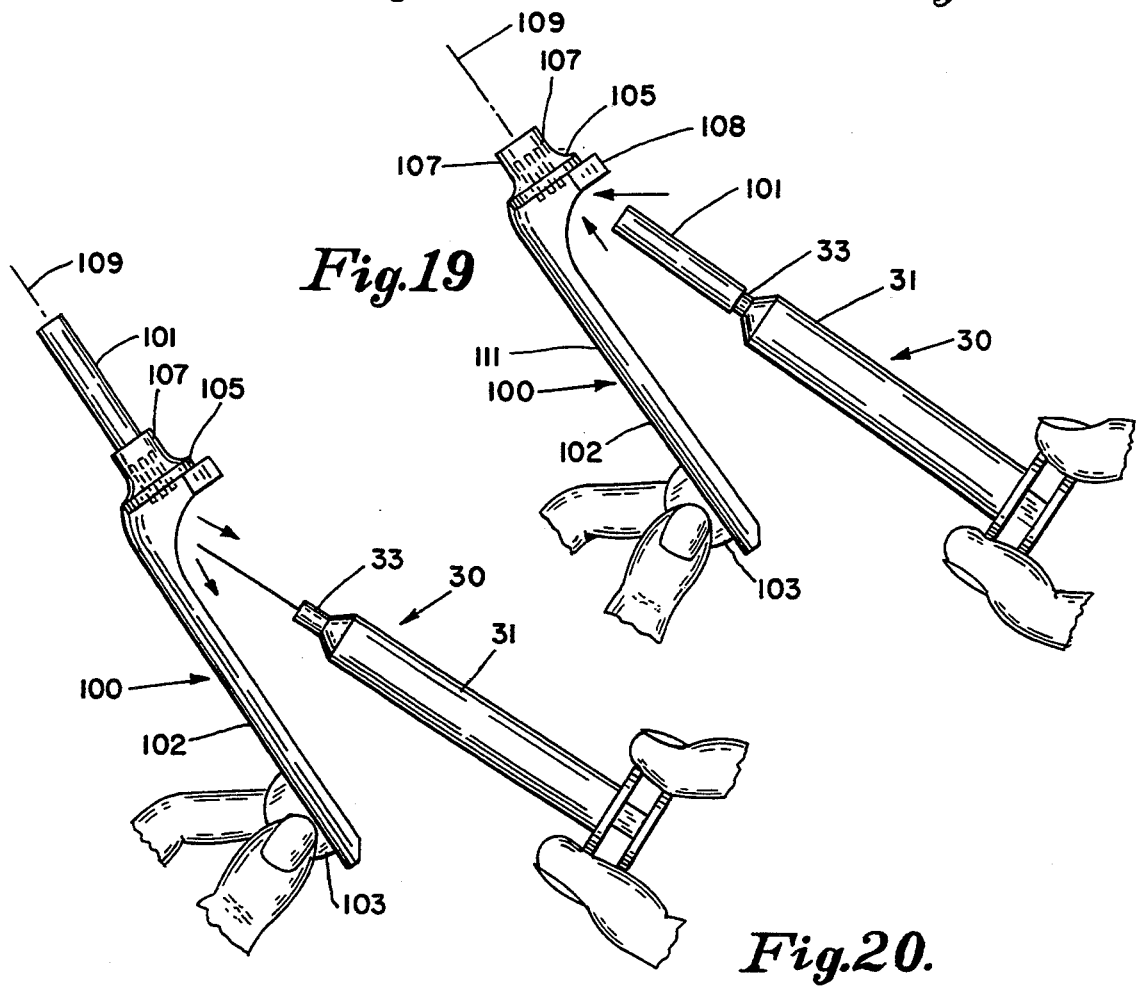
Fig.19
Fig.20.

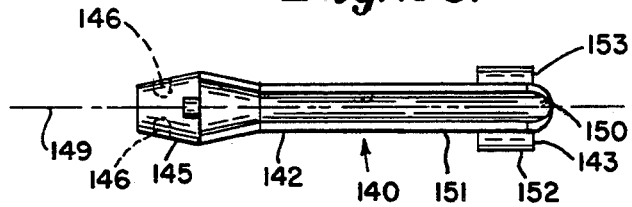
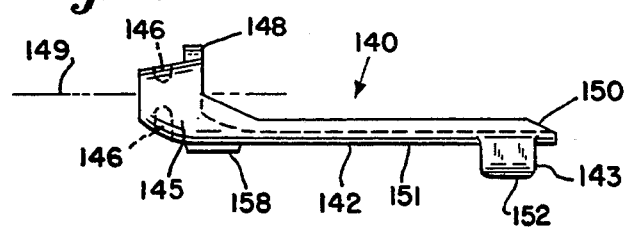
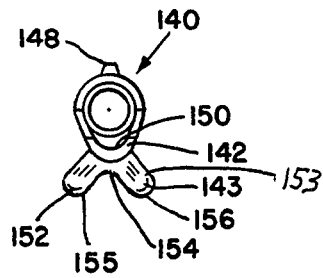
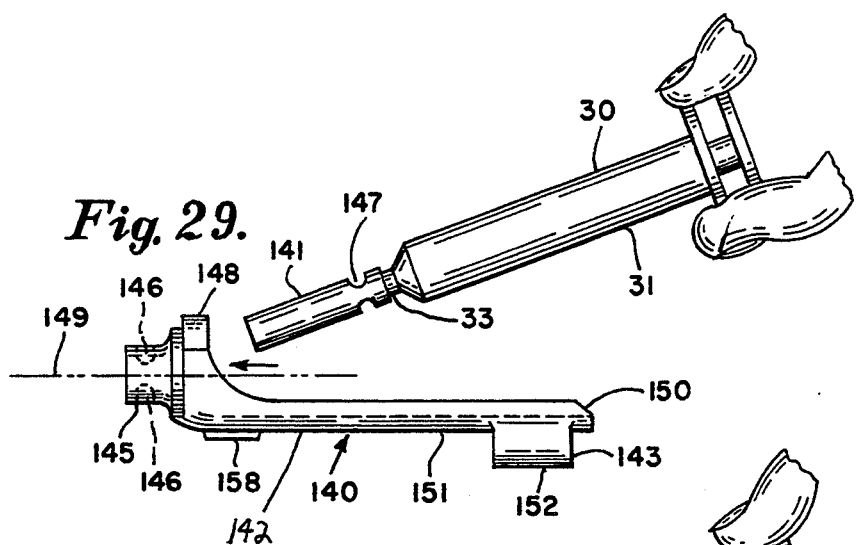
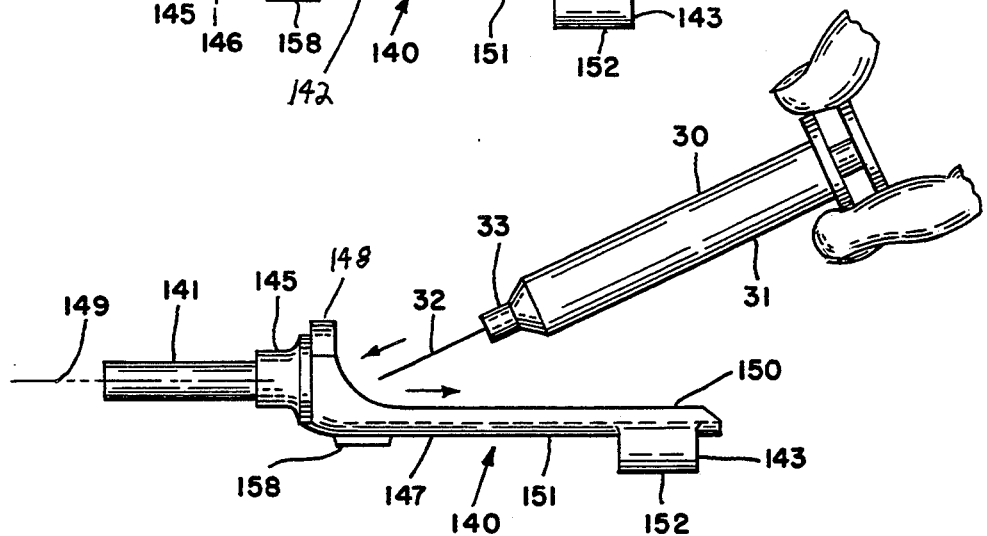

GUARDS FOR HYPODERMIC NEEDLE

CROSS REFERENCE TO RELATED APPLICATION

This application is a continuation-in-part application of Ser. No. 08/004,105, filed Jan. 13, 1993, now abandoned for Improved Guards for Hypodermic Needles. Hypodermic Needles.

BACKGROUND OF THE INVENTION

1. Field of the Invention

This invention generally relates to needle guards for syringes and more particularly to guards that protect attendants from being stuck inadvertently by a hypodermic needle attached to a syringe.

2. Description of Related Art

Medical personnel run a substantial risk of disease transmittal if they are inadvertently stuck by a hypodermic needle after its use. The proliferation of AIDS, hepatitis and related infectious diseases transferred by hypodermic needles has led to the development of various articles for protecting healthcare workers from being stuck inadvertently. Many of these articles include guards or covers for the needle; some attach to the syringe.

U.S. Pat. No. 2,854,976 to Heydrich discloses a protective device for needles of hypodermic syringes. This device has a structure at one end for engaging the proximal end of a syringe needle and a structure for encasing the point of the needle at the distal end. In one embodiment a structure can be disposed intermediate the ends to engage and support the needle. In all embodiments, spaced upper parts of an H-shaped structure engage the syringe needle; diametrically opposed and extending wings of that structure provide a finger grip. An attendant's fingers are brought into proximity to the needle, although not the end of the needle. Moreover, it appears that an attendant must use two hands to hold that syringe and simultaneously operate the H-shaped structure to remove the protective device from the syringe.

U.S. Pat. No. 4,946,447 to Hardcastle et al. discloses a protective cover or sleeve for a hypodermic needle. This protective sleeve includes a formed resilient plastic body split longitudinally to form slightly greater than a semicylinder. The body is snapped onto the barrel of a hypodermic needle before or after the needle is used. It may be slid longitudinally over the needle to protect against accidental puncture by the needle after the needle is used and locks into this position. In order to protect an attendant, the protective cover must be attached to the syringe prior to and during its use.

U.S. Pat. No. 4,985,020 to Kasuya discloses a guard with a finger grip that facilitates the positioning of the guard over a needle. When the guard is positioned properly, a proximate end engages a hub and locks the guard in place. However, a finger grip adjacent the proximal end brings the attendant's fingers into close proximity with the needle.

U.S. Pat. No. 5,026,356 to Smith discloses an open sleeve that attaches to a syringe body and that carries an axially movable L-shaped member and rocker spring. When the L-shaped member moves axially to a distal position, at the tip of the hypodermic needle, the L-shaped member deflects and covers the needle tip under the influence of the rocker spring. At other positions the L-shaped member rests against the side of the needle. This structure does not cover the needle completely so an attendant can still contact portions of the needle. The open sleeve and L-shaped member remains on the needle during use and operation requires two hands.

U.S. Pat. No. 5,092,461 to Adam discloses a needle cover that is adapted for one-handed operation. It has a tip portion for positive engagement with a needle tip to hold the cover in place over a tip end portion of the needle. The needle cover is essentially smooth and has no finger grips for an attendant. In use the guide slides forward or toward the distal end of the needle to release the needle. It slides rearwardly or proximally to cover the needle. The device apparently remains in place on the syringe during use.

U.S. Pat. No. 5,087,249 to Deal discloses a tubular guard that slides over the end of a hypodermic needle to engage a hub on the syringe at the proximal end of the needle. An elongated handle terminates with an angularly disposed head member. The head member includes a cavity for receiving and releasably engaging the syringe cap. A pair of opposed resilient clips, or alternatively, a pair of spaced apart walls interconnected at one end form the cavity. This structure does remove an attendant's hands from proximity to the needle. However, an attendant must use both hands simultaneously to grip the syringe and operate the handle.

The following patents disclose covers in which an axial body attaches to a syringe barrel or to a needle hub at the end of the barrel:

U.S. Pat. No. 2,745,403 to Goldberg discloses a disposable cartridge suitable for containing single dosages of medicaments and the like. The cartridge comprises an elongate, tubular body portion of substantially uniform bore, thickened and partially constricted near one end. An annular groove, formed on the outer surface of the tubular body, can engage a closure collar element. An imperforate disc, adapted to being easily pierced by a hypodermic needle and formed of resilient, liquid impervious material, substantially inert toward and insoluble in liquids, solvents and medicaments commonly administered by injection is positioned normal to the axis of said tubular body portion and overlying the opening in the partially constricted end thereof. An essentially cylindrical hub element having an axially located opening extending therethrough has a radially extending, annular flange at one end, disposed coaxially relative to the tubular body portion with its flanged end against the outside surface of said disc. Means on the hub element engage with and support a double-pointed hypodermic needle with one end of said needle extending through the hub opening and piercing the disc. A closure collar element around the flanged end of the hub element and engaging with the annular groove formed on the tubular body end, presses the disc therebetween to provide a liquid-tight partial closure at the end of the cartridge. A movable piston, within the tubular body portion embraces the walls thereof to provide a liquid-tight closure at the open end of the tubular body portion.

U.S. Pat. No. 3,076,455 to McConnaughey et al. discloses a holder for hypodermic syringe cartridges. The holder is formed as a channel having an opening along one side thereof through which the cartridge may be snapped into and out of the holder by lateral movement. The width of the opening is less than the maximum width of the cartridge, and the channel is formed of a stiff spring material so that the holder may be distorted momentarily to permit the insertion and removal of the cartridge.

U.S. Pat. No. 4,795,443 to Permenter et al. discloses a device for sealing the tip of a syringe needle. A cap has a shank extending to a mount adapted to be slidably held by a syringe barrel. The cap moves in a spring bias contact along a needle body and beyond its tip whereupon it springs into alignment with the tip. The cap can then be moved in a reverse direction to seal the needle in the cap.

U.S. Pat. No. 4,867,746 to Dufresne discloses a needle shield that can be attached to a syringe hub. The shield is flexible and moves out of the way of the needle point for insertion into the skin. The shield has a one-piece construction and includes an elongated hood-like body that surrounds the needle and includes at one end a blunt front end shield and at the other end a mounting ring for frictionally engaging the hub of the needle of the syringe. An integral lock on the body snaps over the needle for holding the shield body over the contaminated needle.

U.S. Pat. No. 4,994,046 to Wesson et al. discloses an elongated cylindrical body portion with a spoon-shaped shield member. The cylindrical body can be snapped around a syringe barrel. The spoon-shaped member extends from the distal end of the body portion and can deflect transversely from a non-use configuration to a slightly deflected in use configuration to permit the needle to extend beyond the spoon-shaped member. When the body portion of the guard slides to an extended position, the spoon-shaped member returns to its undeflected configuration. A plurality of ribs formed on the inner wall of the spoon-shaped member engage the needle end thereby to seal the end of the needle.

U.S. Pat. No. 5,074,848 to Burt et al. discloses a needle receptacle with a sheath having a cradle portion and attached barrel. The cradle portion is open along its top portion and includes parallel spaced-apart protective flanges. The barrel end is tapered into a needle receiving portion and includes a flared connection between the cradle and the barrel end to serve as a guide for needles as they are inserted into the barrel. A detent structure prevents the needle from turning.

In a medical environment, an attendant wants to keep one hand free during an injection process in order to maintain contact with the patient or perform some related function. Thus, it is desirable that an attendant be able to remove and replace any needle cover with one hand.

The previously described Goldberg, McConnaughey et al., Adam and Dufresne patents disclose guards for one-handed operation. However, none of these references provides any mechanism for completely covering the needle to minimize the transfer of disease from the needle by accidental contact. Moreover, the operation of the Dufresne guard brings an attendant's fingers into close proximity with the needle tip. Guards proposed by Smith, Permenter et al. and Wesson et al. remain on the syringe during use. The addition of this structure can complicate the injection process. The Deal and Burt et al. patents disclose guards that fully cover a needle, but they each require two hands for removing and replacing the cover. The Kasuya patent discloses a cover that might be adapted for operation by one hand. However, placing the cover on the needle brings an attendant's fingers into close proximity to the needle.

SUMMARY

Therefore it is an object of this invention to provide a needle guard for a syringe that inherently positions an attendant's fingers remotely from the needle.

Another object of this invention is to provide a guard for a syringe that is easily removed from and replaced onto the needle during the injection process.

Still another object of this invention is to provide a guard for a syringe that is detachable from the syringe.

Yet another object of this invention is to provide a guard for a syringe that can be detached and replaced with one hand.

Yet still another object of this invention is to provide a guard that protects an attendant from disease transfer from a needle by contact with the needle.

In accordance with one aspect of this invention, a syringe guard includes an axially extending open channel body portion that abuts a part of a syringe barrel in a substantially coaxial relationship. A tubular guard portion extends axially from the body portion and is substantially axially coextensive with the needle on the syringe. A finger grip structure extends from the body portion remotely from the tubular guard portion for protecting the user from inadvertently contacting the end of the needle.

In accordance with another aspect of this invention a guard for use with a syringe includes an axially extending tongue that extends from a tubular cover portion and has a circumferential cross section that conforms to a syringe barrel. A tubular cover portion is substantially coextensive with the needle on the syringe. A finger grip structure includes first and second extensions for being grasped by an attendant. These extensions extend from the guard remotely from the tubular cover.

In accordance with still yet another aspect of this invention a guard for use with a syringe includes a tubular cover that is substantially axially coextensive with a needle on the syringe. An axially extending tongue attached to the tubular cover has a circumferential cross section that conforms to the syringe barrel. A thin radial extension adapted for being grasped between two fingers is attached to the body portion remotely from the tubular cover portion and a shield structure connects to the guard for overlying the thin radial extensions thereby to protect a user from inadvertently contacting the end of the needle.

In yet another aspect of this invention, a guard for use with a syringe includes an axially extending open channel body portion for abutting a syringe barrel portion in a coaxial relationship. An annular clasp attaches to one end of the body portion for releasably engaging a needle cover. A gripping structure extends from the body portion remotely from the annular clasp to enable an attendant to grasp the structure remotely from the tubular cover.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a top view of one embodiment of a guard constructed in accordance with this invention;

FIG. 2 is a side view of the guard shown in FIG. 1;

FIG. 3 is an end view of the guard shown in FIG. 1;

FIG. 4 is a view of the guard shown in FIGS. 1 through 3 positioned for application on a syringe;

FIG. 5 is a view of the guard as shown in FIGS. 1 through 3 in a covering position on the syringe;

FIG. 11 is a top view of still another embodiment of a guard constructed in accordance with this invention;

FIG. 12 is a side view of the guard shown in FIG. 11;

FIG. 13 is an end view of the guard shown in FIG. 11;

FIG. 14 is a view of the guard shown in FIGS. 11 through 13 positioned for application on a syringe;

FIG. 15 is a view of the guard as shown in FIGS. 11 through 13 in a covering position on the syringe;

FIG. 16 is a top view of yet another embodiment of a guard constructed in accordance with this invention;

FIG. 17 is a side view of the guard shown in FIG. 16;

FIG. 18 is an end view of the guard shown in FIG. 16;

FIG. 19 is a view of the guard shown in FIGS. 16 through 18 positioned for application on a syringe with a needle cover;

FIG. 20 is a view of the guard as shown in FIGS. 16 through 18 in a position in which the needle cover is removed from the syringe;

FIG. 26 is a top view of still yet another embodiment of a guard constructed in accordance with this invention;

FIG. 27 is a side view of the guard shown in FIG. 26;

FIG. 28 is an end view of the guard shown in FIG. 26;

FIG. 29 is a view of the guard shown in FIGS. 26 through 28 positioned for application on a syringe with a specially formed needle cover; and FIG. 30 is a view of the guard as shown in FIGS. 26 through 28 in a position in which it stores the cover and the syringe is removed from the cover.

DESCRIPTION OF ILLUSTRATIVE EMBODIMENTS

Figure 6:
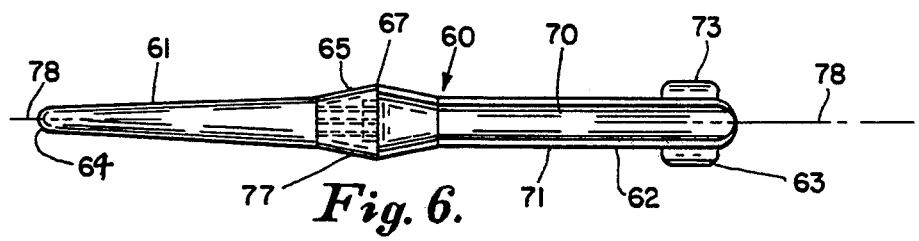
FIG. 6 is a top view of another embodiment of a guard constructed in accordance with this invention.

FIGS. 1 through 5 disclose one embodiment of a guard for a syringe that is constructed in accordance with this invention. As shown particularly in FIGS. 4 and 5, a syringe 30 includes a barrel 31 and a hypodermic needle 32 that attaches to a hub 33 formed at one end of the barrel 31 that is a "distal" end. An attendant displaces a plunger 34 at a "proximal" end toward the distal end by grasping and moving the plunger 34 with his or her fingers 35, as shown in FIG. 4, to inject a patient. The syringe 30 lies along a syringe axis 36.

A plastic guard 40 constructed in accordance with this embodiment by injection or other plastic molding techniques includes a tubular cover 41 that extends axially from a guard body 42 for being substantially axially coextensive with the needle 32 on the syringe 30. A finger grip 43 extends radially from the guard body 42 to provide a structure that an attendant can easily grab.

More specifically, the tubular cover 41 has a closed end 44. A hub gripping portion 45 at the proximal end of the tubular cover 41 comprises, in this embodiment, a plurality of radially inwardly extending teeth 46 as shown in FIG. 3. These teeth 46 frictionally engage the hub 33 when the hub gripping portion 45 overlies the hub 33 as shown in FIG. 5.

The guard body 42 comprises an axially extending, cylindrically shaped plate or member 47 with an inner surface 50 that abuts a portion of and conforms to the syringe barrel 31 so it overlies a part of the syringe barrel 31. This member 47 serves as part of an open-channel body portion for abutting the syringe barrel 31. A link 51 extends axially between the tubular cover 41 and the guard body 42 and terminates with a radially offsetting curved portion 52 that attaches to and supports the tubular guard 41 and hub engaging portion 45. The offsetting curved portion 52 aligns the tubular cover 41 with the needle 32 when the guard body 42, particularly the member 47, engages the syringe barrel 31.

If the syringe 30 is to be used for administering medication, an attendant initially will prepare the syringe by filling the syringe 30 by conventional procedures. Specifically the attendant grasps the syringe barrel 31 or plunger 34 with his or her fingers 35 and the finger grip 43 with fingers 53 as shown in FIG. 4. When the attendant places the guard body 42 that is adjacent the finger grip 43 against the syringe barrel 31, his or her fingers 53 are spaced a significant distance from the needle 32, particularly its free end. This initial alignment as shown in FIG. 4 therefore occurs without requiring the attendant to move his or her fingers 43 into close proximity with the needle 32. Although this procedure generally will be implemented using two hands, it normally is a procedure that the attendant performs remotely from the patient, so a two-handed operation is not required.

As a next step, or an initial step if blood is to be drawn into the syringe the attendant grasps the syringe 30 in one hand and, with the thumb or other fingers of that same hand, engages and displaces the finger grip 43 axially toward the needle 32 until the hub engaging portion 45 clears the hub 33. Then the attendant can tip the syringe 30 downwardly so gravity pulls the guard 40 from the needle 32.

Covering the needle 32 after use can also be accomplished with one hand. The attendant places the syringe 30 on a horizontal support surface. Then with one hand the attendant grasps the finger grip 43 and positions the guard 40 on the syringe 30 so the tubular cover 41 partially encases the needle 32. Next, the attendant can lift the syringe 30 and the guard 40 off the support surface and, grasping the syringe 30 and the finger grip 43 simultaneously, move the guard 40 proximally toward the plunger until the hub engaging portion 45 overlies the syringe hub 33. As an alternative, the attendant could place the guard 40 on the support surface and, holding the syringe barrel 31, slide the tip of the needle 32 into the tubular cover 41. Then the attendant could lift the syringe 30 and guard 40 off the support surface and complete the installation as previously described.

The guard 40 therefore minimizes the chances that the attendant will be stuck by a needle inadvertently during each of these operations. In each, the attendant's fingers are located at the radial extension 43 that is remote from the tubular cover 41. Thus, the attendant's fingers are always spaced from the needle 32 by a distance equal to the axial length of the link 51 and its radial offsetting portion 52. Moreover, the cover 41 encases the needle completely. This tubular guard 40 is detachable from the syringe 30 during an injection and the guard 40 can be removed and replaced using one hand.

FIGS. 6 through 10 disclose another embodiment of a guard for a syringe 30 that is constructed in accordance with another aspect of this invention. In this embodiment a plastic guard 60 constructed by injection or other plastic molding techniques includes tubular or cover 61 that extends axially from a guard body 62 for being substantially coextensive with the needle 32 on the syringe 30. A finger grip 63 extends essentially tangentially from the guard body 62 to provide a structure that an attendant can easily grab.

Figure 10:
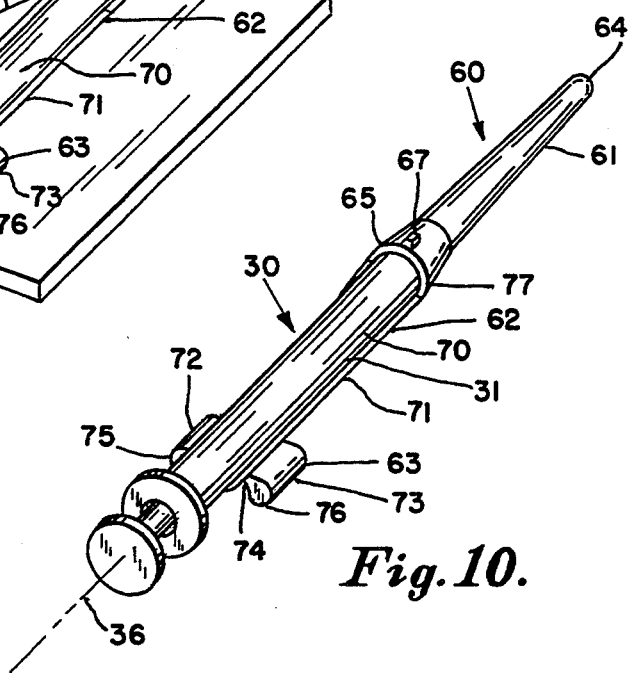
FIG. 10 is a view of the guard as shown in FIGS. 6 through 8 in a covering position on the syringe.
Figure 21:
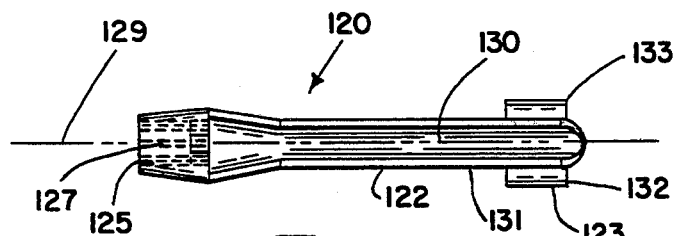
FIG. 21 is a top view of yet still another embodiment of a guard constructed in accordance with this invention.
Figure 22:
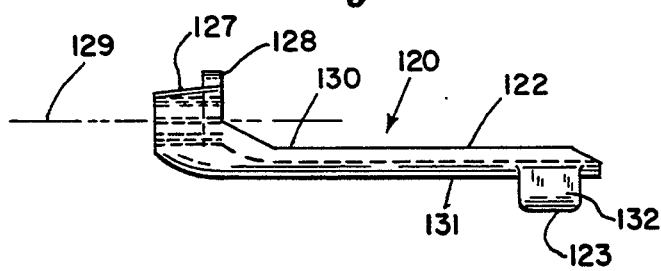
FIG. 22 is a side view of the guard shown in FIG. 20.

More specifically, the tubular cover 61 has a closed end 64. A hub gripping portion 65 at the proximal end of the tubular cover 61 comprises, in this embodiment, a plurality of radially inwardly extending teeth 66 shown in FIG. 8. These teeth 66 frictionally engage the hub 33 when the hub gripping section 65 overlies the hub 33 as shown in FIG. 10.

The hub gripping portion 65 also constitutes an annular transition portion that is intermediate the guard body 62 and the tubular cover 61. It additionally has a radial extending pivot 67 that is positioned diametrically opposite from a connection point 68 at which the tubular cover 61 and guard body 62 join.

The guard body 62 has an inner arcuate or cylindrically shaped surface 70 along an axial extension or tongue 71. The inner surface 70 is adapted to abut a portion of and conform to the syringe barrel 31 so the tongue 71 overlies a part of the syringe barrel 31. A finger grip 63 facilitates the attendant's ability to grasp the guard 60. In this particular embodiment the finger grip 63 comprises two finger grips 72 and 73 that extend essentially tangentially and transversely with respect to the tongue 71. As particularly shown in FIG. 8, the fingers 72 and 73 can be joined and shaped with a depression 74 whereupon the fingers 72 and 73 produce discrete resting points 75 and 76 respectively.

Figure 8:
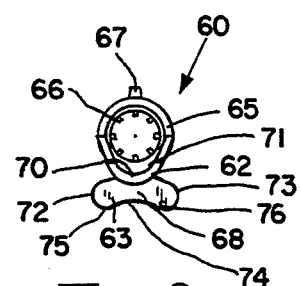
FIG. 8 is an end view of the guard shown in FIG. 6
Figure 8A:
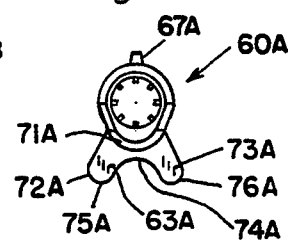
FIG. 8A depicts variations of the guard shown in FIG. 8.

FIG. 8A depicts an alternate structure for the guard 60, particularly the finger grip 63 shown in FIG. 8. More specifically, a finger grip 63A in FIG. 8A comprises two finger grips 72A and 73A that extend more radially from the tongue 71A than tangentially and transversely as the finger grips 72 and 73 in FIG. 8. A depression 74A between the fingers 72A and 73A produces discrete resting points 75A and 76A respectively.

Figure 7:
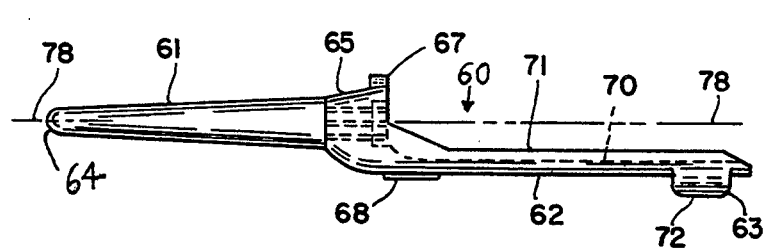
FIG. 7 is a side view of the guard shown in FIG. 6.
Figure 9:
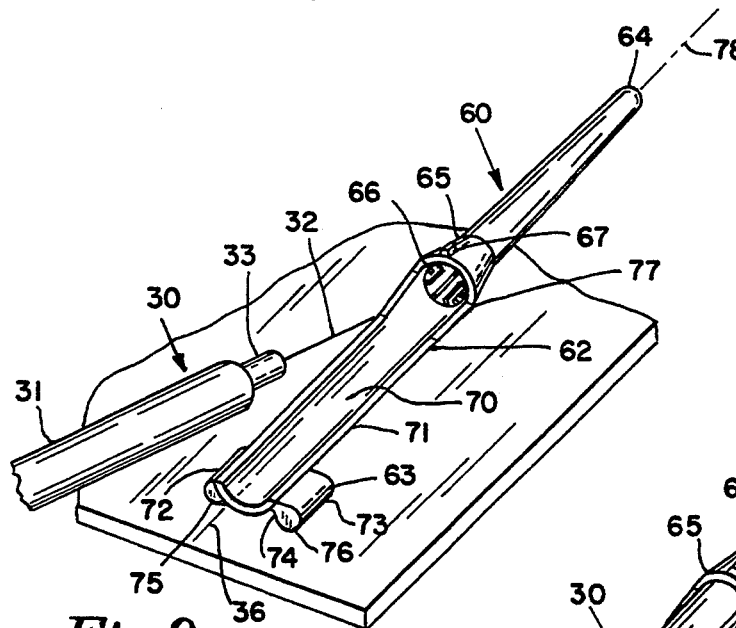
FIG. 9 is a view of the guard shown in FIGS. 6 through 8 positioned for application on a syringe.

Either of the constructions shown in FIGS. 8 or 8A positions the center of gravity approximately at a position identified by reference numeral 77 in FIGS. 7, 9 and 10. Consequently this guard 60 always lands in a "face up" position on a horizontal surface as shown in FIG. 9. In this position the inner surface 70 is at the top of the tongue 71 and the resting points 75 and 76 (or 75A and 76A) lie on a surface. If the cover were to fall in any other position, the center of gravity and pivot points formed by the ends of the finger grips 72 and 73 (or 72A and 73A) or the radial pivot 67 (or 67A in FIG. 8A) turn the guard 60 about its longitudinal axis 78 to the position shown in FIG. 9.

In use an attendant will fill the syringe 30 by conventional procedures. The attendant then merely lays the guard 60 on a support surface as shown in FIG. 9. As previously indicated, regardless of how the attendant places the guard 60 on the surface, it assumes the position shown in FIG. 9. Then the attendant can slide the needle 32 into the tubular cover 61 at the annular transition section or hub engaging section 65. When the needle is partially or nearly fully inserted into the tubular cover 61, the attendant can tip the syringe 30 and elevate the needle 32. Then with one hand the attendant can grasp the syringe 30 and the finger grips 72 and 73 (or 72A and 73B in FIG. 8A) and pull the guard 60 axially along the syringe barrel 31 until the hub engaging portion 65 engages the hub 33 and locks the guard 60 in place as shown in FIG. 10. When the attendant is ready to use the syringe, the attendant grasps the syringe 30 in one hand and, with the thumb or other fingers of that same hand, engages and displaces the finger grips 72 and 73 (or 72A and 73A in FIG. 8A) axially toward the needle 32 until the hub engaging portion 65 clears the hub 33. Then the attendant can tip the syringe 30 downwardly so gravity pulls the guard 60 from the needle 32. Again, as the guard 60 drops to a support surface, it moves into the position shown in FIG. 9 and is positioned to be replaced on the syringe. The process for replacing the guard 60 is the same as described above with respect to covering the needle after an initial filling operation.

The guard 60 therefore minimizes the chances that the attendant will be stuck by a needle inadvertently during each of these operations. In this particular embodiment, the attendant's fingers are located at the finger grips 72 and 73 (or 72A and 73A) that are remote from the tubular cover 61. Thus, the attendant's fingers are always spaced from the needle 32 by a distance equal to the axial length of the tongue 71. The tubular cover 61 encases the needle 32 completely. This particular embodiment also facilitates the attachment and removal of the guard 60 with one hand, particularly as the guard 60 will always fall into a position as shown in FIG. 9 when dropped on a horizontal support. The ease of removal has the further benefit of detaching the guard 60 during its use.

FIGS. 11 through 15 disclose still another embodiment of a guard 80 constructed in accordance with still another aspect of this invention. In this particular embodiment a plastic guard 80 includes a tubular cover 81 that extends axially from a guard body 82 for being substantially axially coextensive with the needle 32 on the syringe 30. A finger grip structure 83 extends from the guard body 82 to provide a structure that an attendant can easily grab.

More specifically, the tubular cover 81 has a closed end 84. A hub gripping portion 85 at the proximal end of the tubular cover 81 comprises, in this embodiment, a plurality of radially inwardly extending teeth 86 as shown in FIG. 13. These teeth 86 frictionally engage the hub 33 when the hub gripping portion 85 overlies the hub 33 as shown in FIG. 5.

The tubular cover 81 and guard body 82 lie along a guard axis 87. The guard body 82 provides an inner cylindrically shaped surface 90 as a part of an open substantially semicylindrical channel or cradle 91 that forms around the axis 87. The inner surface 90 abuts a portion of and conforms to the syringe barrel 31 so the cradle 91 overlies a part of the syringe barrel 31.

The finger grip structure 83 includes two axially extending finger shields 92 and 93 extending substantially radially and transversely from cradle 91. Each of the finger shields 92 and 93 lies along and is curved about an axis parallel to the guard axis 87 to form a partially cylindrical surface that conforms somewhat to the shape of attendant's fingers.

A thin radial finger grip 94 extends in a plane essentially normal to a plane through the finger shields 92 and 93. An arcuately formed transverse member 95 extends transversely to the axis 87 at the distal end of the finger grip 94.

When the attendant is ready to remove the guard 80, the attendant grasps the syringe 30 in one hand 96 as shown in FIG. 15. The attendant can then either remove the cover 80 using his or her other hand 97 or, as previously described, use the thumb or other fingers on his or her hand 96 to slide the guard 80 distally and axially until the hub engaging portion 85 clears the hub 33. At that point the attendant can tip the syringe 30 downwardly so gravity pulls the guard 80 from the needle 32.

Covering the needle 32 after a filling operation or use can be accomplished using two hands 96 and 97 as shown in FIG. 14. Alternatively, the attendant can position the guard 80 on a surface in a position as shown in FIG. 12, and partially insert the needle 32 into the tubular cover 81. Next the attendant can lift the syringe 30 and the guard 80 off the support surface and, grasping the syringe and the finger grips 94 and/or 95 move the guard 80 proximally toward the plunger until the hub engaging portion 85 overlies the syringe hub 33.

The guard 80 therefore minimizes the chances that the attendant will be stuck by a needle inadvertently during each of these operations. In this particular embodiment, the attendant's fingers are located at the finger grips 94 and 95. Thus, the shields 92 and 93 form a solid barrier between the attendant's fingers and the needle 32. Moreover, in this particular embodiment the attachment and removal of the guard 80 to a syringe 30 can be accomplished with one hand.

FIGS. 16 through 20 disclose yet another embodiment of a guard for a syringe 30. In this particular embodiment, a plastic guard 100 is adapted to engage a standard tubular cover 101 that is shipped as a protective cover for a needle 32 on a syringe 30. In this specific embodiment, the guard 100 includes a guard body 102, a gripping structure 103 and a cover engaging section 105.

More specifically, the cover engaging section 105 at the distal end of the guard body 102 comprises a plurality of inwardly extending teeth 106 as shown in FIG. 18. These teeth 106 frictionally engage the exterior surface of the tubular cover 101. The cover engaging section 105 additionally includes a distally extending cylindrical support section 107 that carries the teeth 106 axially to provide sufficient friction between the guard 100 and the cover 101 to overcome the friction that exists between the tubular cover 101 and the hub 33.

The cover engaging portion 105 additionally includes a transversely extending inverted triangular stabilizer 108 that extends in a direction oppositely from the gripping structure 103 and normal to a guard axis 109. This stabilizer 108 limits rotation of the guard 100 about the guard axis 109 when it is placed on a horizontal support surface so that an inner cylindrical surface 110 of the guard body 102 is always generally facing in an upward direction. An open channel or cradle 111 forms the surface 110 that abuts the syringe barrel 31 in a substantially coaxial relationship.

To remove the cover 101, an attendant grips the finger grip 103, that extends radially from the proximal end of the body 102, and slides the guard 100 over the tubular cover 101 from the distal end of the syringe. As the cover 101 is in place, this operation poses no risk to the attendant. The attendant then pulls the guard 100 proximally along the syringe 30 until the clasping structure 105 reaches the vicinity of the hub 33.

When the attendant then grasps the finger grip 103 and slides the guard 100 distally, the guard 100 carries the tubular cover 101 off the needle 32 as shown in FIG. 20. The assembled guard 100 and cover 101 then have a configuration which is somewhat similar to the structure shown in FIGS. 1 through 5.

When the guard 100 and assembled cover 101 are placed on a surface, the finger grip 103 acts as a pivot and the stabilizer 108 allows only limited rotation of the guard 100 about its axis 109 so the cylindrical surface 110 is accessible. An attendant can cover the needle 32 after use by inserting the needle 32 into the tubular cover 101 or by placing the syringe 30 on a surface, grasping the combined guard 100 and cover 101 by the finger grip 103 and partially inserting the needle 32 into the tubular cover 101. Next the attendant can lift the syringe 30 and guard 100 off a support surface and, grasping the syringe 30 and the finger grip 103 simultaneously, move the guard 100 proximally along the syringe barrel 31 until the tubular cover 101 covers the needle 32. It is also possible to throw the syringe 30 and guard 100 away.

The guard 100 also minimizes the chance that attendant will be stuck by a needle inadvertently during each of these operations. As the guard is applied, the needle 32 is covered by the tubular cover 101. As the tubular cover 101 is removed and subsequently replaced with the guard 100, the attendant's fingers are always spaced from the needle 32 by a distance equal to the length of the guard body 102. Finally it is possible to remove and replace the cover 101 with one hand.

FIGS. 21 through 25 disclose yet another embodiment of a guard for a syringe 30 that serves the function of the guard shown in FIGS. 16 through 20 and incorporates certain features of the guard shown in FIGS. 6 through 10. A plastic guard 120 is adapted to engage a standard tubular cover 121 that is shipped as a protective cover for a needle 32 on a syringe 30. The guard 120 includes a guard body 122, a gripping structure 123 and a cover engaging section 125.

Figure 23:
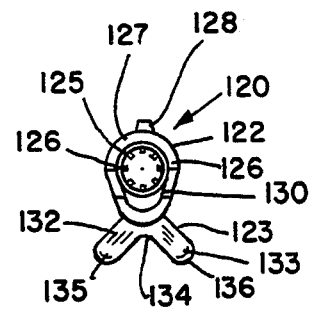
FIG. 23 is an end view of the guard shown in FIG. 20.
Figure 24:
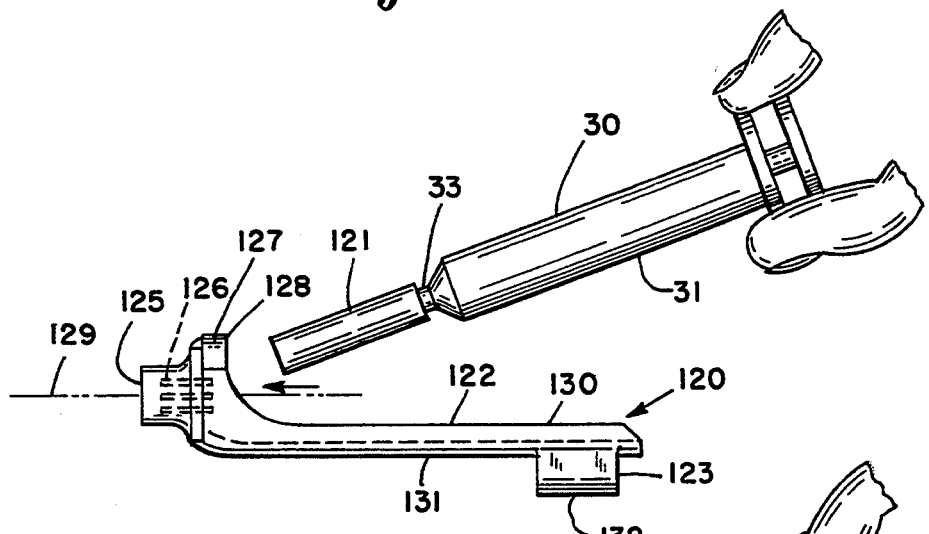
FIG. 24 is a view of the guard shown in FIGS. 21 through 23 positioned for application on a syringe with a conventional needle cover.
Figure 25:
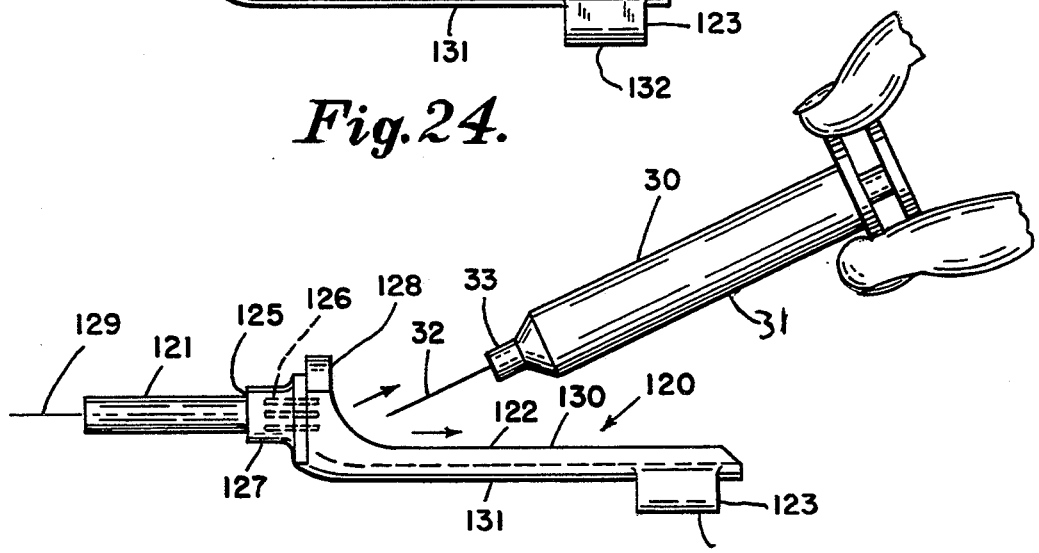
FIG. 25 is a view of the guard as shown in FIGS. 21 through 23 in a position in which it stores the cover and the syringe is removed from the cover.

The cover engaging section 125 at the distal end of the guard body 122 comprises a plurality of inwardly extending teeth 126 as shown in FIG. 23 and in phantom in FIGS. 24 and 25. These teeth 126 frictionally engage the exterior surface of the tubular cover 121 that, in turn, functionally engages the syringe hub 33. The cover engaging section 125 includes a distally extending cylindrical support section 127 that carries the teeth 126 axially to provide sufficient friction between the guard 120 and the cover 121 to overcome the friction that exists between the tubular cover 121 and the hub 33.

A radially extending pivot 128 on the cover engaging portion 125 extends in a direction oppositely from the gripping structure 123 and normal to a guard axis 129. This pivot 128 serves the same function as the pivot 67 in FIGS. 6 through 10.

Still referring to FIGS. 21 through 25, a semicylindrical surface 130, formed by an elongated open channel or cradle, abuts the syringe barrel 31 in a substantially coaxial relationship. The finger grip 123 facilitates the attendant's ability to grasp the guard 120 and comprises two finger grips 132 and 133 that extend essentially radially with respect to the guard axis 129. As particularly shown in FIG. 23, the fingers 132 and 133 join about a depression 134 and produce discrete resting points 135 and 136 respectively. With this construction, the guard 120 always lands in a "face up" position on a horizontal surface as shown in FIGS. 24 and 25. In this position the inner surface 130 is at the top of the cradle 131 and the resting points 135 and 136 lie on a surface. If the cover were to fall in any other position, the center of gravity and pivot points formed by the ends of the finger grips 132 and 133 and the radial pivot 128 would turn the guard 120 about its longitudinal axis 129 to the position shown in FIGS. 24 and 25.

To remove the cover 121, an attendant grips the finger grip 123, that extends radially from the proximal end of the body 122, and slides the guard 120 over the tubular cover 121 from the distal end of the syringe 30. As the cover 121 is in place, this operation poses no risk to the attendant. The attendant then pulls the guard 120 proximally along the syringe 30 until the clasping structure 125 reaches the vicinity of the hub 33. When the attendant then grasps the finger grip 123 and slides the guard 120 distally, the guard 120 carries the tubular cover 121 off the needle 32 as shown in FIG. 25. The assembled guard 120 and cover 121 then have a configuration which is somewhat similar to the structure shown in FIGS. 1 through 5 and FIGS. 6 through 10.

When the guard 120 and assembled cover 121 are placed on a surface, the finger grip 123 and pivot 128 assure that the guard 120 will rest in the orientation shown in FIG. 25 so the cylindrical surface 130 is accessible. An attendant can cover the needle 32 after use by inserting the needle 32 into the tubular cover 121 or by placing the syringe 30 on a surface, grasping the combined guard 120 and cover 121 by the finger grip 123 and partially inserting the needle 32 into the tubular cover 121. Next the attendant can lift the syringe 30 and guard 120 off a support surface and, grasping the syringe 30 and the finger grip 123 simultaneously, move the guard 120 proximally along the syringe barrel 31 until the tubular cover 121 fully covers the needle 32.

The guard 120 minimizes the chance that attendant will be stuck by a needle inadvertently during each of these operations. As the guard 120 is applied, the needle 32 is covered by the tubular cover 121. As the tubular cover 121 is removed and subsequently replaced with the guard 121, the attendant's fingers are always spaced from the needle 32 by a distance equal to the length of the guard body 122. Finally it is possible to remove and replace the cover 121 with one hand.

The different guards shown in FIGS. 16 through 20 and FIGS. 21 through 25 rely upon the friction between two sliding surfaces to establish a connection to a conventional needle cover and a guard. FIGS. 26 through 30 depict an embodiment of a guard 140 and a specially formed needle cover 141 that provides a more positive connection.

The guard 140 includes a guard body 142, a gripping structure 143 and a cover engaging section 145. The cover engaging section 145 at the distal end of the guard body 142 comprises a pair of inwardly and circumferentially extending ribs 146. These ribs 146 have some resilience and slide over the exterior surface of the tubular cover 141. When the ribs 146 reach corresponding grooves 147 near the proximal end of the cover 141, the ribs 146 expand and snap into the grooves 147. This resulting detent action provides a positive connection and indication, by touch and sound, that the cover 141 is fully seated in the guard 140. Subsequent distal movement of the guard 140 will necessarily remove the cover 141 from the needle 32.

The cover engaging portion 145 includes a radially extending pivot 148 that cooperates with the gripper structure 143 in the same way the pivot 128 and gripping structure 123 cooperate in the embodiment of FIGS. 21 through 25.

Still referring to FIGS. 26 through 30, a semicylindrical surface 150, formed by an elongated open channel or cradle 151, abuts the syringe barrel 31 in a substantially coaxial relationship. The finger grip extension 143 facilitates the attendant's ability to grasp the guard 140 and comprises two finger grips 152 and 153 that extend essentially radially with respect to the axis 149 like the finger grips 123 in FIGS. 21 through 25. The fingers 152 and 153 join to form a depression 154 and define resting pints 155 and 156 respectively. A pad 158 with a planar surface provides additional stability by virtue of its surface and of a slight lowering of the center of gravity of the guard 140. Consequently this guard 150 also always lands in a "face up" position on a horizontal surface as shown in FIGS. 29 and 30.

The embodiment of FIGS. 26 through 30 operates in essentially the same manner as the embodiment of FIGS. 21 through 25 with the same results and advantages. The major difference is the positive connection between the ribs 146 and slots 147 that is not overcome or broken unless a significant separating force is applied. Any such force greatly exceeds the forces that would occur during normal use.

Each of the embodiments shown in FIGS. 1 through 30 therefore provide a guard that protects an attendant from being stuck inadvertently by a hypodermic needle. In each it is possible to remove and replace a needle cover with one hand. During each such operation, the attendant's fingers are kept clear of the needle 32, particularly the needle tip. In certain of the embodiments, particularly as shown in FIGS. 6 through 30, the guards are formed to lie in a predetermined range of positions thereby to facilitate cover replacement.

It will also be apparent that a number of modifications can be made to these specifically disclosed embodiments. For example, the stabilizer structure shown in FIGS. 16 through 20 could be added to the guard shown in FIGS. 1 through 5. Each of these structures has been shown as being constructed by plastic injection molding. Other materials and methods could be used to form each specific embodiment or variations thereof. The structure for engaging a syringe hub has been shown as inwardly radially extending teeth. Other structures could be formed to provide the frictional engagement.

It will be apparent that these and other modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A guard for use with a syringe that includes an axially extending barrel portion, a hub portion formed at one end of the barrel portion and means for attaching an axially extending needle to the hub portion and with a tubular cover for covering the needle, said guard being formed as an integral unit comprising:
   A. an axially extending tongue with a circumferential cross-section that conforms to the syringe barrel and that is adapted for abutting a part of the syringe barrel portion in a substantially coaxial relationship therewith,
   B. syringe engagement means located at a first axial end of said tongue for effecting a connection between the syringe and said guard, and
   C. gripping means located at the second axial end of said tongue for facilitating the attachment and removal of said guard from said syringe thereby to protect a user from inadvertently contacting the end of the needle.

2. A guard as recited in claim 1 wherein the tubular cover engages the syringe hub portion and said syringe engagement means includes means for frictionally engaging the tubular cover.

3. A guard as recited in claim 1 wherein the tubular cover frictionally engages the syringe hub portion and includes first connection means thereon and said syringe engagement means includes second connection means for engaging said first connection means on the tubular cover thereby to provide a positive connection between said guard and the tubular cover means.

4. A guard as recited in claim 1 wherein said annular transition section includes a radial pivot extending therefrom diametrically opposite from the connection of said annular transition section and said tongue, the mass of each of said transition and annular body portions being selected to position the center of gravity of said guard and the connection of said annular transition section and said tongue.

5. A guard as recited in claim 4 wherein the radius of curvature of said circumferential surface is greater than the radius of said tubular cover portion and wherein said gripping means includes first and second thin extensions extend tangentially from said tongue for being grasped by a user.

6. A guard for use with a syringe that includes an axially extending barrel portion, a hub portion formed at one end of the barrel portion, an axially extending needle attached to the hub portion and a tubular needle cover for covering the needle, said guard being formed as an integral unit comprising:
   A. an axially extending, open channel body portion for abutting the syringe barrel portion in a substantially coaxial relationship therewith,
   B. annular clasping means attached to one end of said body portion transversely to the axis of said body portion for releasably engaging the needle cover, and
   C. gripping means extending from a portion of said body portion remote from said annular clasping means and proximate another end of said body portion.

7. A guard as recited in claim 6 wherein said axial body portion is formed as a tongue extending from said clasping means with a circumferential cross-section that conforms to the syringe barrel and wherein said gripping means comprises at least one radial extension adapted for being grasped between two fingers.

8. A guard as recited in claim 7 additionally comprising position stabilizing means extending from said annular transition portion for preventing rotation of said guard on a surface, said stabilizing means including a transverse planar extension from said annular transition portion having a planar edge spaced from said annular transition portion for engaging the surface.

* * * * *